United States Patent [19]
Rowland et al.

[11] Patent Number: 5,427,115
[45] Date of Patent: Jun. 27, 1995

[54] APPARATUS FOR STRICTURE DIAGNOSIS AND TREATMENT

[75] Inventors: Christopher A. Rowland, Marlborough; M. Joshua Tolkoff, Brookline; Ella Zaslavsky, Marblehead, all of Mass.

[73] Assignee: Boston Scientific Corporation, Natick, Mass.

[21] Appl. No.: 120,475

[22] Filed: Sep. 13, 1993

[51] Int. Cl.⁶ ............................................. A61B 10/00
[52] U.S. Cl. .................................... 128/756; 128/799
[58] Field of Search ............... 128/749, 750, 751, 752, 128/753, 754, 755, 756, 757; 604/189

[56] References Cited

U.S. PATENT DOCUMENTS

| | | | |
|---|---|---|---|
| 2,955,591 | 10/1960 | MacLean | 128/756 |
| 3,613,664 | 10/1971 | Willson et al. | |
| 4,227,537 | 10/1980 | Suciu et al. | 128/756 |
| 4,235,244 | 11/1980 | Abele et al. | 128/749 |
| 4,653,510 | 3/1987 | Koll | 128/759 X |
| 4,662,381 | 5/1987 | Inaba | 128/756 |
| 4,763,670 | 8/1988 | Manzo | 128/756 |
| 4,850,373 | 7/1989 | Zatloukal et al. | 128/749 |
| 4,850,957 | 7/1989 | Summers | 604/22 |
| 4,946,440 | 8/1990 | Hall | 604/95 |
| 4,966,162 | 10/1990 | Wang | 128/750 |
| 5,201,323 | 4/1993 | Vermeulen | 128/756 |
| 5,217,023 | 6/1993 | Langdon | 128/756 |

*Primary Examiner*—Sam Rimell
*Attorney, Agent, or Firm*—Pearson & Pearson

[57] ABSTRACT

Apparatus for use in the diagnosis and treatment of strictures in a biliary duct, urinary tract or pancreatic tract. The apparatus includes a dual lumen catheter device. One lumen size is sized to accommodate a guidewire. A second, parallel lumen has a non-circular cross-section and carries a cytology brush at one end that couples through an operator to a manipulator at another end. The cytology brush has an effective diameter that is greater than the diameter of the catheter device. Brush cytology samples are obtained without removing the guidewire from a stricture and without introducing any relative motion between the guidewire and the catheter. As the cytology brush is retracted into the non-circular lumen, its bristles compact around the operator for storage within the lumen. A predetermined arrangement of markers at the distal end of the catheter facilitates the measurement of stricture length by direct endoscopic visualization.

21 Claims, 3 Drawing Sheets

APPARATUS FOR STRICTURE DIAGNOSIS AND TREATMENT

BACKGROUND OF THE INVENTION

1. Field of the Invention

This invention generally relates to the diagnosis and treatment of strictures in biliary ducts and urinary or pancreatic tracts and more particularly to apparatus that is useful in such diagnoses and treatment.

2. Description of Related Art

If a stricture forms in an individual's biliary duct, urinary tract or pancreatic tract, flow through the duct or tract can stop. One step used in the diagnosis and treatment of symptoms resulting from such a stricture is a determination of whether the cells in the stricture are malignant. One methodology for diagnosing such malignancy involves brush cytology performed for example, by a cytology brush apparatus as described in U.S. Pat. No. 4,763,670. Thereafter the physician may place a stent in the vessel to open or dilate the stricture. Apparatus for placing such a stent is described in U.S. Pat. No. 5,234,457.

During the diagnosis and treatment of a stricture in the biliary duct, urinary and pancreatic tracts, a physician initially introduces an endoscope with viewing and working channels through various vessels to position the distal end of the endoscope closely adjacent the proximal side of the stricture. In this discussion the phrases "proximal" and "distal" are applied in terms of the apparatus and the physician. Consequently the proximal end of the apparatus is located externally of the patient for direct manipulation by the physician. Next the physician may perform endoscopic retrograde cholangiopancreatography (ERCP) or transhepatic cholangiography (THC) in the biliary tree or retrograde cystography in the urinary tract. The physician may, prior to or during such procedures, locate the stricture by the injection of contrast media. In addition, the physician may advance an ERCP cannula or similar catheter-like device through the stricture either over a previously placed guidewire or independently of a guidewire.

U.S. Pat. No. 4,763,670 discloses a cytology brush apparatus that is adapted for being advanced through the working channel of an endoscope. This apparatus has a single lumen that receives a standard cytology brush. Consequently the physician must remove any previously located cannula and guidewire from the stricture before using the cytology brush apparatus. Removing the cannula or guidewire has the undesired effect of eliminating any dilation through the stricture that the guidewire has achieved, often only after an extended time and completion of a tedious procedure. It therefore becomes necessary to advance the cytology brush at least partially through the stricture to obtain a sample at an appropriate location without the benefit of any access that the guidewire had established.

Alternatively it might be possible to lead a catheter-like device partially through the stricture over a guidewire that extends through the stricture then remove the guidewire to allow a cytology brush to be transported through the catheter-like device. However, to regain whatever access the catheter-like device has preserved, the cytology brush must be retracted through the length of the catheter device so the guidewire can be reintroduced. Withdrawing a cytology brush through the length of such a catheter-like device can deposit all or most of the sample on the interior surface of the catheter-like device. Consequently physicians normally will withdraw the guidewire, use the cytology brush apparatus, remove the cytology brush apparatus with the catheter-like device and then reintroduce the guidewire through the stricture.

The length of any stent used to dilate a stricture should correspond closely to the length of the stricture. A physician currently views a two-dimensional image of the stricture obtained by fluoroscopy or X-ray imaging and will use the imaged endoscope to estimate the stricture length. If the stricture lies entirely in the plane of the image, this process provides a reasonably accurate estimate of stricture length. However, in most cases the stricture does not lie in the plane of the image, so any such estimate will be incorrect. Consequently physicians tend to estimate length based upon information obtained by scaling an image and intuitive knowledge of the anatomy. This usually results in placing a stent that is longer than necessary.

After the guidewire has been reintroduced and a stent of appropriate length has been selected, the physician introduces a stent delivery system such as is disclosed in U.S. Pat. No. 5,234,457, over the guidewire and into the stricture. Once located, the stent expands and dilates the stricture. Next the physician can remove the stent delivery system, the guidewire and the endoscope to complete the procedure.

As previously indicated, this procedure has several disadvantages that can be summarized as follows. The guidewire must be removed during the various procedures thereby losing any access through stricture. The procedure incorporates several steps that can prolong the procedures. The selection of stent length is imprecise.

U.S. Pat. Nos. 4,235,244, 4,850,957, 4,966,162 and 5,217,023 disclose other prior art cytology brush apparatus for obtaining samples through the working channel of an endoscope. Each of these patents discloses a cytology brush with a plug of water-soluble material that closes a distal end of an outer catheter body to prevent contamination of an inner cavity body and the brush during its introduction into the body. U.S. Pat. No. 4,235,244 obtains a sample on the ends of the bristle brushes that are withdrawn into a protective sheath. U.S. Pat. Nos. 4,850,957 and 4,966,162 and 5,217,023 flush recovered samples debrided from tissue by a brush. None of these cytology brushes discloses any structure for enabling cytology brush apparatus to be used in conjunction with a guidewire or any method for estimating stent length. Consequently each cytology brush apparatus disclosed in these patents introduces the same complexities and operates with the same disadvantages as previously indicated.

U.S. Pat. Nos. 3,613,664 and 4,946,440 disclose cytology brushes with self-contained steerable guidewires while U.S. Pat. Nos. 4,227,537 and 4,662,381 disclose cytology brushes that are self-contained primarily for collecting samples from the cervix. None of these patents, other than U.S. Pat. No. 4,946,440, discloses any use in the diagnosis and treatment of strictures in the biliary duct or the pancreatic or urinary tracts. None is adapted for use with a standard guidewire. U.S. Pat. Nos. 3,613,664 and 4,662,381 and 4,946,440 also do not disclose or suggest any structure for estimating stent length requirements.

U.S. Pat. No. 4,227,537 discloses a brush apparatus for collecting sample tissue from an endometrial cavity to aid in diagnosing endometrial cancer. The apparatus includes a catheter-like device with a graded scale that allows a physician to determine the location of each sample with respect to some reference point. However, this patent does not disclose or suggest any method for estimating the length of a stricture with particular reference to determining stent length.

U.S. Pat. No. 5,201,323 discloses a wire-guided cytology brush that has a flexible outer sheath with a lumen for accepting a flexible inner sheath. A brush or similar tissue gathering device is located at the distal end of the inner sheath. The inner sheath has a lumen therethrough for passing over a guidewire. First and second handles at the proximal ends of the inner and outer sheaths manipulate the inner and outer sheaths respectively. A retainer clip maintains the relative positioning of the inner sheath within the outer sheath during insertion and removal of the brush assembly over the guidewire.

This apparatus does permit a physician to obtain tissue samples from within a stricture without having to remove a guidewire. However, the path of any cytology brush apparatus, including the cytology brush shown in this patent, is a tortuous path. At each of various bends along the path, the guidewire and inner sheath come into contact and produce friction during relative movement between the inner sheath and guidewire. Thus if a physician holds the outer sheath handle in a fixed position with one hand while manipulating the inner sheath with the other, it is possible for the movement of the inner sheath to move the guidewire. Any such motion should be avoided. Moreover, the requirement of removing and reinstalling the retainer clip before and after a sample is taken further complicates the physician's procedure.

SUMMARY

Therefore it is an object of this invention to provide apparatus useful in the diagnosis and treatment of strictures adapted for use with a conventional endoscope and guidewire.

Another object of this invention is to provide apparatus useful in the diagnosis and treatment of strictures that obtains cell samples from the stricture without requiring the removal of a guidewire.

Still another object of this invention is to provide apparatus useful in the diagnosis and treatment of strictures that obtains cell samples from the stricture without requiring the removal of a guidewire and without introducing any guidewire motion.

Yet still another object of this invention is to provide apparatus useful in the diagnosis and treatment of strictures that is useful in estimating the length of the stricture.

Still yet another object of this invention is to provide apparatus useful in the diagnosis and treatment of strictures that simplifies the procedures needed to obtain a sample of tissue.

Yet still another object of this invention is to provide apparatus useful in the diagnosis and treatment of strictures that simplifies the procedures needed to obtain a sample of tissue and to estimate the length of the stricture.

Yet still another object of this invention is to provide apparatus useful in the diagnosis and treatment of strictures that is relatively easy to manufacture and cost effective.

In accordance with one aspect of this invention, apparatus that is adapted to obtain a tissue sample from a stricture includes a catheter with a first lumen for sliding over a guidewire extending through a stricture and a second lumen that houses a cytology brush and cytology brush operator. The operator includes a manipulator for enabling the cytology brush to be extended from and retracted into one end of the catheter at the stricture to obtain a cell sample. As this manipulation occurs in the second lumen it does not produce any relative motion between the catheter and the guidewire.

In accordance with another aspect of this invention, a catheter having a first lumen for sliding over a guidewire extending through a stricture includes a radiopaque marker at one end that passes through the stricture and a plurality of markers formed on the catheter in predetermined spaced patterns that extend from the one end of the catheter for a distance exceeding the maximum stricture length. The physician then can visualize the patterns that remain visible on the other side of the stricture to through the viewing channel of an endoscope to determine the length of the passage through the stricture.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
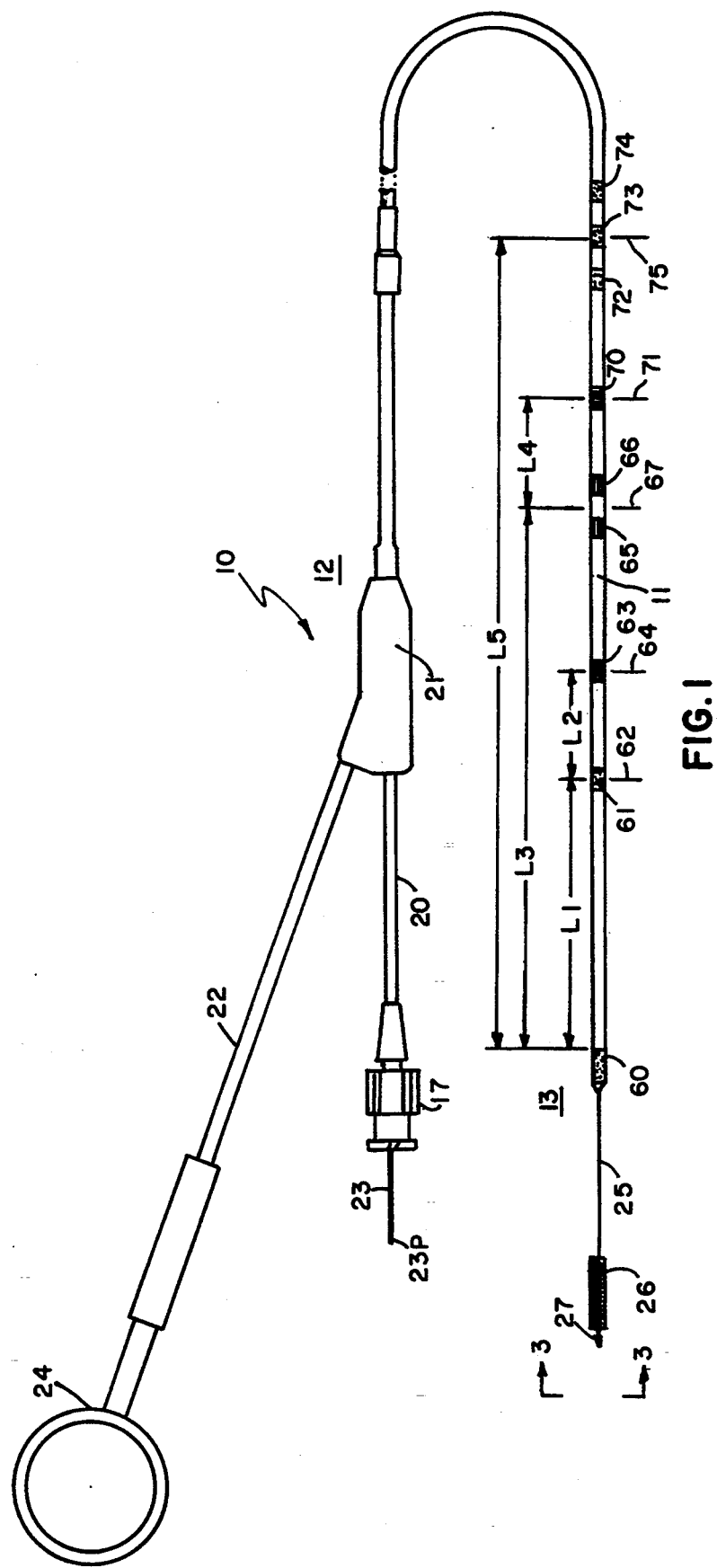
FIG. 1 is a plan view of apparatus constructed in accordance with this invention.

FIG. 1 discloses apparatus 10 that is useful in the diagnosis and treatment of a stricture and that embodies this invention. The apparatus 10 comprises a catheter 11, such as an 8F catheter having an overall diameter of about 2.6 mm. If the apparatus 10 is designed for use in the biliary duct, urinary tract and pancreatic tract, the catheter 11 generally will have an overall length of about 200 cm between a proximal end 12 located exteriorly of the patient and a distal end 13. As shown more particularly in FIG. 2, the catheter 11 has a first lumen 14 with a circular cross-section and a second lumen 15 with a non-circular cross-section. The lumen 14 is an extension of a passage that extends from a Leur lock fitting 17 and through a first tubular arm 20 and hub 21 to communicate with the lumen 14 in the catheter 11. A second tubular arm 22 extends from the hub 21 and has an internal passage that communicates with the second lumen 15. The interconnection of tubular arms 20 and 22 through the hub 21 to communicate with the respective lumens 14 and 15 is well known in the art. A guidewire 23 extends through the lumen 14, a portion of the guidewire 23 being shown as extending from the Leur lock fitting 17.

Figure 4:
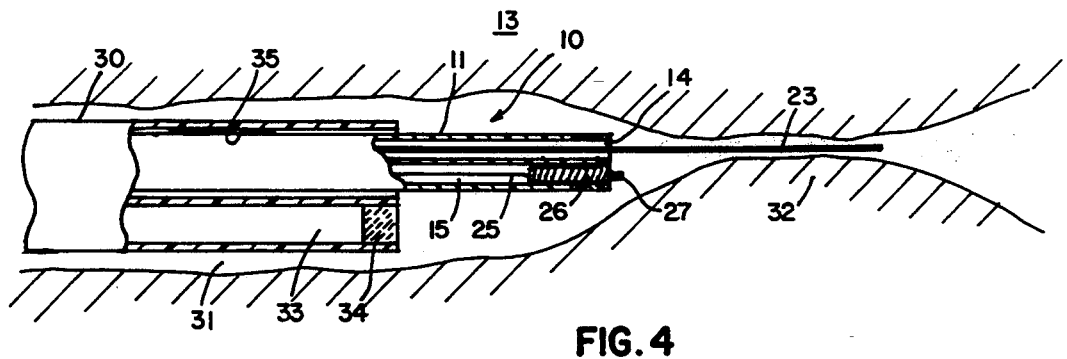
FIG. 4 is a view of a vessel and apparatus constructed in accordance with this invention.

A ring manipulating handle 24 connects to a wire operator 25 that extends through the passage in the tubular arm 22, the hub 21 and the lumen 15 to carry at its distal end a standard cytology brush 26 and an end tip 27. FIG. 1 discloses the cytology brush in an extended position in which the physician has moved the manipulator 24 toward the distal end 13. FIG. 4 depicts the cytology brush 26 after the physician retracts the manipulator 24 (FIG. 1) so that the cytology brush 26 lies in the second lumen 15 so the catheter 11 forms a protective sheath.

If the guidewire 23 is prepositioned in a patient, a physician can advance the apparatus 10, with the cytology brush 26 retracted into the lumen 15, over the guidewire. Specifically, the physician can lead the lumen 14 at the distal end 13 of the apparatus 13 onto the proximal end 23P of the guidewire 23. Then the physician can advance the apparatus 10 distally into the patient.

FIG. 4 illustrates certain advantages of this invention. As shown in FIG. 4, an endoscope 30 is located in a vessel 31, such as a common bile duct, urinary tract or pancreatic tract having a stricture 32. The endoscope 30 has an illumination channel (not shown, but well known in the art), a viewing channel 33 represented by an optical window 34 and an working channel 35. As shown in FIG. 4, the endoscope 30 is spaced slightly proximally of the stricture 32. The catheter 11 lies in the working channel 35 and has been advanced over the guidewire 23 that extends through the stricture 32 thereby to provide access through the stricture 32.

Thus as will be apparent from FIG. 4, the catheter 11 has positioned the cytology brush 26 proximate the stricture 32. The guidewire 23 remains in the patient and the catheter 11 can advance over the guidewire 23.

Figure 5:
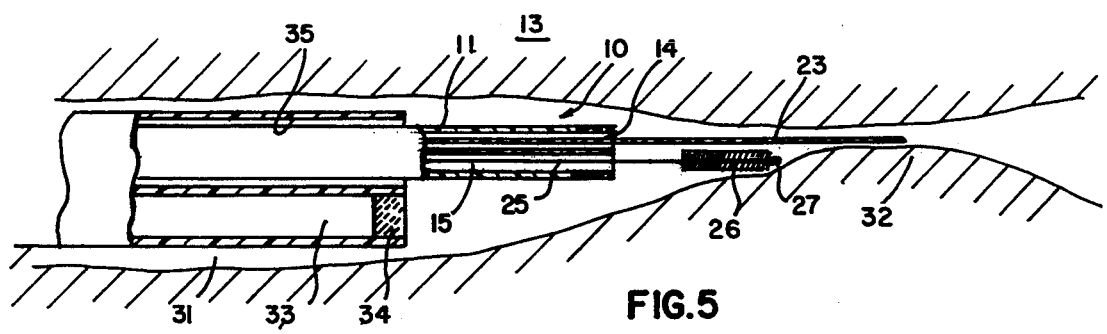
FIG. 5 is another view of the apparatus according to this invention extended partially through the stricture of FIG. 4.

Referring to FIG. 1, a physician will obtain a cell sample by grasping the proximal end of the apparatus 10 as, for example, at the hub 21 to advance the apparatus 10 over the guidewire 23 and partially into the stricture 32 through the access the guidewire 23 provides. Next the physician advances the manipulator 24 distally to extend the cytology brush 26 from the lumen 15. Referring to FIG. 5, when this occurs, the cytology brush 26 engages the surface of the stricture 32 and recovers cell samples. Next the physician retracts the handle 24 shown in FIG. 1 to retract the cytology brush 26 into the lumen 15 so it has an orientation as shown in FIG. 4. At this time, the physician can withdraw the catheter 11 leaving the guidewire 23 in place and retaining the access through the stricture 32.

As with any apparatus, the endoscope 30 and catheter 11 will lie along a tortuous path. Consequently contact between the operator 25 and the walls of the catheter 11 forming the lumen 15 will produce friction. However, the generation of this friction does not produce relative motion between the guidewire 23 and the catheter 11 because the guidewire 23 lies in the first lumen 14 that is parallel to, but independent of, the second lumen 15. Thus, motion of the operator 25 while a cell sample is being obtained does not introduce any motion between the guidewire 23 and catheter 11.

Figure 3:
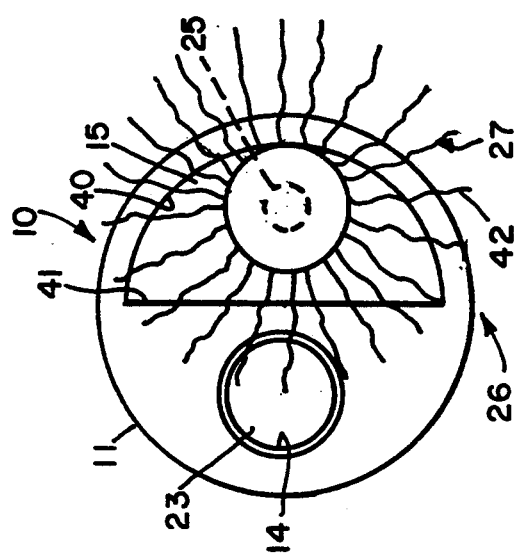
FIG. 3 is an end view of the apparatus taken along lines 3—3 in FIG. 1.
Figure 2:
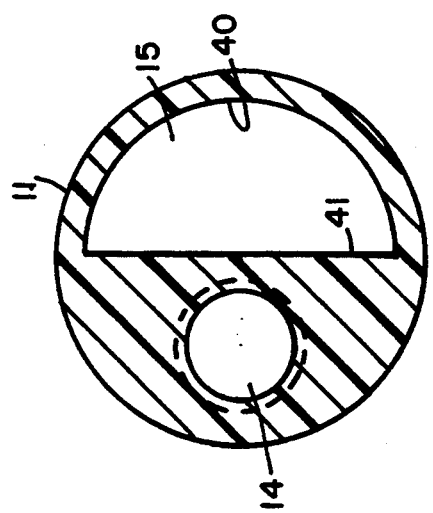
FIG. 2 is a cross-section of a catheter used in constructing the apparatus shown in FIG. 1.
Figure 6:
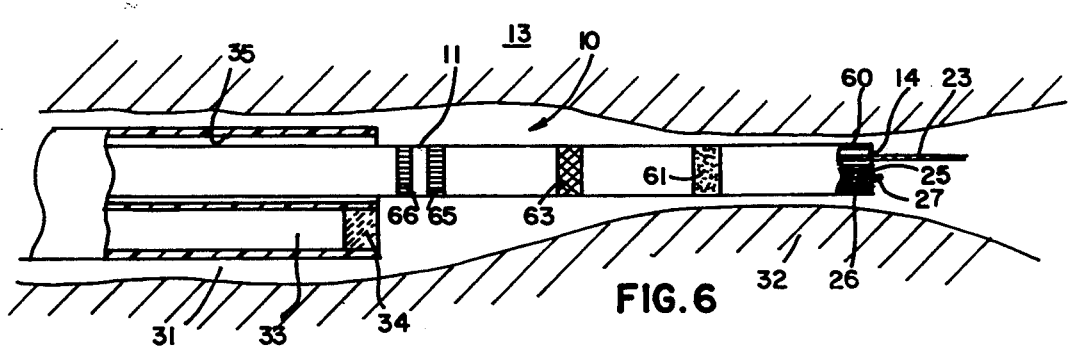
FIG. 6 is still another view of the apparatus of this invention extended through the stricture of FIG. 4.

FIGS. 4 through 6 depict a guidewire 23 with a diameter that is much smaller than the diameter of the lumen 14. This is for purposes of explanation only. The actual differences in diameters is about 0.1 mm. In a typical apparatus 10 the lumen 14 has a diameter of about 1.0 mm to accommodate a 0.9 mm guidewire (i.e., a standard 0.035" guidewire). In addition, the lumen 15 has a non-circular cross-sections. FIGS. 2 and 3 depict one embodiment in which the lumen 15 has an essentially semicircular cross-section with a maximum opening (i.e., horizontally in FIGS. 2 and 3) of about 1 mm. This opening accommodates the 0.9 mm end tip 27 and centers the end tip 27 in the lumen 15 (i.e., vertically in FIGS. 2 and 3. Generally the net cross-sectional area of the lumen 15 (i.e., its total area minus the cross-sectional area of the operator 25 and the end tip 27) provides a sufficient volume for storing the bristles 42 in a compacted form. More specifically the lumen 15 has a cylindrical wall portion 40 and a planar wall portion 41 that, as shown in FIGS. 2 and 3, lies on a diameter through the catheter 11. The size of the lumen 15 can be increased by angling the surface 41 to produce angularly displaced, radial walls 41A and 41B as shown in FIG. 3.

As also shown in FIG. 3 that is a view looking proximally to the apparatus 10 from beyond the distal end 13 of the apparatus 10 with the cytology brush 26 extended, the cytology brush 26 comprises bristles 42 that extend radially from the operator 25. In one particular embodiment, the bristles have an approximate radius of 1.5 mm. Thus, the bristles 42 terminate along a circumference that has a diameter (i.e., 3.0 mm.) that exceeds the overall diameter of the catheter 11 (i.e., 2.6 mm.). As shown in FIG. 3, the bristles 42 radiate from a center line that is centered in the lumen 15 and offset from the center of the catheter 11. As the cytology brush 26 is retracted into the lumen 15, the individual bristles will deflect axially of the catheter 11 and fill those portions of the lumen 15 that lie around the operator 25 (shown by a dashed line in FIG. 3) and in those portions of the lumen on either side of the end tip 27. Consequently, as previously indicated, the cytology brush can have an effective diameter of 3 mm for improved cell gathering and still fit within a catheter 11 having a smaller diameter in the order of 2.6 mm and an even smaller non-circular lumen 15.

Figure 7:
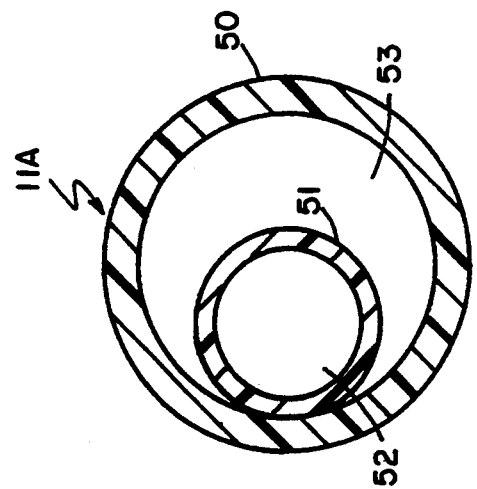
FIG. 7 is a cross-sectional view of another embodiment of the catheter shown in FIGS. 2 and 3.

The catheter 11 shown in FIGS. 2 and 3 can be manufactured with integrally formed lumens 14 and 15 by conventional extrusion processes. It is also possible to manufacture a catheter with parallel lumens by inserting a smaller tube in a longer tube. FIG. 7 discloses one such catheter 11A with an outer tube 50 having an outer diameter corresponding to the other diameter of the catheter 11 in FIG. 2. A second tube 51 in FIG. 7 has a lumen with the same diameter as the lumen 14. The tubes 50 and 51 in FIG. 7 have wall thicknesses corresponding to the wall thicknesses of the catheter 11 in FIG. 2. This construction in FIG. 7 produces a guidewire lumen 52 through the smaller tube 51 that can accommodate a standard guidewire and a second, non-circular lumen 53 for carrying a cytology brush that can be the same size or fuller than the cytology brush 26 shown in FIG. 3. Both the embodiments shown in FIGS. 2 and 3 and in FIG. 7 therefore provide a structure whereby the catheter 11 or 11A can accommodate a cytology brush having a cross-section that is larger than possible with a lumen having a circular cross-section.

Referring to FIGS. 1 and 6 the catheter 11 includes a radiopaque marker 60 at its distal end 13. Additional markers formed on the catheter 11 in predetermined patterns with predetermined spacings from the radiopaque marker 60 permit the physician to visualize the structure length. These patterns vary in terms of the arrangement of one or more markers in groups and in the color of the markers. In one specific example, the radiopaque marker 60 is blue. The remaining markers need not be radiopaque, and a next marker comprises a single blue mark 61. The mark 61 is located on a center line 62 at a distance $L_1$ from the marker 60. A next proximally located black marker 63 is positioned on a center line 64 at a distance $L_2$ from the center line 62. Two spaced green markers 65 and 66 closely adjacent a center line 67 form a next mark that is located a distance $L_3$ from the radiopaque marker 60. A next single black marker 70 has a center line 71 located at a distance $L_4$ from the center line 67. A final group of three blue markers 72, 73 and 74 are located with respect to a center line 75 that is a distance $L_5$ from the radiopaque marker 60. As one example, the spacings are:

$L_1 = 5$ cm; $L_2 = 2$ cm; $L_3 = 10$ cm; $L_4 = 2$ cm; and $L_5 = 15$ cm.

Each marker, such as marker 61, has an axial length of 4 mm and markers in a group, such as the group formed by markers 65 and 66 and the group formed by markers 72, 73 and 74 have an intermarker spacing of 4 mm.

This or other spacings provide the physician with the ability to determine stricture length by viewing the catheter 11 through the viewing channel of an endoscope. More specifically, other imaging techniques used during the normal course of diagnosis and treatment will verify the location of the radiopaque marker 60 distally of the stricture 32. Then the physician looks through the viewing channel 33 of the endoscope 30 in FIG. 6. If the radiopaque marker 60 has advanced through the stricture 32 from the position shown in FIG. 4 to the position shown in FIG. 6, the markers 62 and 63 are located in the stricture 32 and are not visible. However, the physician will be able to observe the double green markers 65 and 66. This allows the physician to determine that the stricture 32 is approximately 10 cm long. The use of different patterns and colors enhances this visualization particularly when the viewing channel 34 has a narrow depth of field. The physician will be able to discriminate the patterns and colors even when they are out of focus. Moreover this measurement is obtained without the need for additional fluoroscopy or other radiation dependent imaging so that both the physician, staff and patient are spared unnecessary radiation exposure.

Still referring to FIG. 6, once this visualization is complete, the physician can withdraw the catheter 11 still leaving the guidewire 23 in place. Then apparatus such as disclosed in U.S. Pat. No. 5,234,457 can be transferred along the guidewire 23 and properly located within the stricture 32 to allow the expansion of a stent into the walls of and dilation of the stricture 32 and return of flow through the duct 31.

Thus in accordance with several objects of this invention, the catheter device 11 provides apparatus that is useful in the diagnosis and treatment of strictures in conjunction with conventional endoscopes and guidewires. The apparatus enables diagnosis and treatment without removing the guidewire after access through a stricture has been established. Cytology samples are obtained by a brush located in a lumen that parallels a guidewire lumen. Thus, the cytology samples are obtained without introducing any relative motion between the guidewire 23 and the catheter 11. Moreover retaining the guidewire 23 in the stricture 32 allows the catheter 11, with its unique marking patterns, to advance through the stricture 32 whereupon the physician can, by direct visualization through the endoscope 30, view the marking bands and determine the effective length of the stricture and required length for a stent. Moreover, the surface area of the cytology brush can be increased over that which could otherwise be accommodated in a circular lumen.

This invention has been disclosed in terms of a particular embodiment with an 8F catheter 11 with a diameter of 2.6 mm., a lumen 14 having a diameter of about 1.0 mm. for receiving a standard 0.035" guidewire having a diameter of about 0.9 mm. and a lumen 15 for receiving a brush having an effective working diameter of 3 mm. The catheter with its lumens and cytology brush can be adapted for construction with larger or smaller sizes for appropriate applications or, as apparent from FIG. 7, with differently formed lumens and catheter constructions.

It will be apparent that any such modifications or other modifications can be made to the specifically disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. Cytology brush apparatus for being introduced over a guidewire into a living body to obtain a cell sample, said apparatus comprising:
   A. flexible catheter means for being positioned in the living body, said catheter means terminating at a distal end, first lumen means for allowing said catheter means to slide over the guidewire and second lumen means for providing a second channel in said catheter means, said first and second lumen means comprising first and second lumens, respectively, that extend through said catheter means and through the distal end thereof,
   B. cytology brush means for obtaining a cell sample from the living body wherein said cytology brush means is independent of said first and second lumens, operator means extending through said second lumen,
   C. for supporting said cytology brush means, said operator means including manipulation means for enabling said cytology brush means to be extended beyond the distal end of said catheter means from said second lumen and to be retracted into said second lumen of said catheter means independently of the guidewire disposed in said first lumen to obtain the cell sample.

2. Cytology brush apparatus as recited in claim 1 wherein said first and second lumens are formed as independent parallel lumens in said catheter means.

3. Cytology brush apparatus as recited in claim 2 wherein said first lumen has a cross section corresponding to the cross section of a guidewire and said second lumen has a non-circular cross section.

4. Cytology brush apparatus as recited in claim 3 wherein said second lumen has an essentially semicircular cross section.

5. Cytology brush apparatus as recited in claim 4 wherein said brush comprises radially extending bristles and a distal end tip, said distal end tip having a diameter for passing through the center of said second lumen.

6. Cytology brush apparatus as recited in claim 5 wherein said catheter means has a given outside diameter, said brush bristles, when extended from said second lumen, expanding to a working diameter that is greater than the said catheter means diameter.

7. Cytology brush apparatus as recited in claim 1 additionally including adjacent the distal end of said catheter means a plurality of markers on said catheter means arranged in a predetermined pattern wherein said catheter means comprises a flexible catheter.

8. Cytology brush apparatus as recited in claim 7 additionally including a radiopaque marker at the distal end of said catheter, said predetermined pattern including the organization of said markers into a predetermined arrangement of groups of at least one marker wherein different groups of markers have different visual appearances so that location of the radiopaque marker proximate a selected interior portion of the body yields a direct measurement therebetween by visual observation of said markers interiorly of the body.

9. Cytology brush apparatus as recited in claim 8 said different visual appearances include variations in the color of different markers.

10. Apparatus for obtaining a cell sample from a living body and for being used in conjunction with an endoscope with a working channel and a guidewire extending through the working channel, said apparatus comprising:
   A. flexible catheter means for being positioned in the body over the guidewire, said catheter means terminating at a distal end, first lumen means for allowing said catheter means to slide over the guidewire in the working channel and second lumen means, parallel and spaced from said first lumen means, for providing a second channel in said catheter means, said first and second lumen means comprising first and second lumens, respectively, that extend through said catheter means and through the distal end thereof,
   B. cytology brush means for obtaining a cell sample from the living body wherein said cytology brush means is independent of said first and second lumens,
   C. operator means extending through said second lumen, for supporting said cytology brush means adjacent the distal end of said catheter means, said operator means including manipulation means at the other end for enabling said cytology brush means to be extended beyond the distal end of said catheter means from said second lumen and to be retracted into the distal end of said catheter means independently of the guidewire disposed in said first lumen to obtain the cell sample.

11. Apparatus as recited in claim 10 wherein said first and second lumens are formed as independent parallel lumens in said catheter means.

12. Apparatus as recited in claim 11 wherein said first lumen has a cross section corresponding to the cross section of a guidewire and said second lumen has a non-circular cross section.

13. Apparatus as recited in claim 12 wherein said second lumen has an essentially semicircular cross section.

14. Apparatus as recited in claim 13 wherein said brush comprises radially extending bristles and a distal end tip, said distal end tip having a diameter for passing through the center of said second lumen.

15. Apparatus as recited in claim 14 wherein said catheter means has a given outside diameter, said brush bristles, when extended from said second lumen, expanding to a working diameter that is greater than the said catheter means diameter.

16. Apparatus as recited in claim 10 wherein the endoscope also includes a viewing channel for viewing exteriorly of the working channel proximate a distal end of the endoscope and said catheter means additionally includes adjacent its distal end a plurality of markers arranged in a predetermined pattern ones of said markers visually perceivable through the viewing channel of the endoscope.

17. Apparatus as recited in claim 16 additionally including a radiopaque marker at end of said catheter means, said predetermined pattern including the organization of said markers into a predetermined arrangement of groups of at least one marker wherein different groups of markers have different visual appearances.

18. Apparatus as recited in claim 17 wherein said different visual appearances include variations in the color of different markers.

19. Apparatus as recited in claim 10 wherein catheter means additionally includes adjacent its distal end a plurality of markers arranged in a predetermined pattern.

20. Apparatus as recited in claim 19 wherein predetermined pattern includes the organization of said markers into a predetermined arrangement of groups of at least one marker and wherein different groups of markers have different visual appearances.

21. Apparatus as recited in claim 20 wherein said different visual appearances include variations in the color of different markers.

* * * * *